United States Patent [19]

France et al.

[11] 4,198,311
[45] Apr. 15, 1980

[54] SKIN CONDITIONING TOILET BAR

[75] Inventors: James R. France, Overland Park; Fred Baiocchi, Prairie Village, both of Kans.; Lawrence J. Murphy, Kansas City, Mo.; John L. Van Haften, Overland Park, Kans.

[73] Assignee: C. J. Patterson Company, Kansas City, Mo.

[21] Appl. No.: 921,779

[22] Filed: Jul. 3, 1978

[51] Int. Cl.$^2$ .................. C11D 1/04; C11D 1/83; C11D 3/46; C11D 3/48
[52] U.S. Cl. .................. 252/117; 252/89.1; 252/132; 252/134; 252/174; 252/174.18; 252/174.21; 252/541; 252/557; 252/DIG. 1; 252/DIG. 5; 252/DIG. 16
[58] Field of Search .......... 252/89, 117, 132, 541, 252/557, 174, DIG. 16, 134, 174.18, 174.21, 89.1, DIG. 1, DIG. 5; 424/312

[56] References Cited

U.S. PATENT DOCUMENTS

| 2,733,252 | 1/1956 | Thompson | 260/410.9 |
| 2,789,992 | 4/1957 | Thompson | 260/410.9 |
| 3,523,089 | 8/1970 | Garrett | 252/174 X |
| 3,728,447 | 4/1973 | Osipow | 424/70 |
| 3,846,326 | 11/1974 | Wright | 252/107 |
| 3,988,255 | 10/1976 | Seiden | 252/107 |
| 4,012,341 | 3/1977 | Orshitzer | 252/548 |
| 4,029,606 | 6/1977 | Isa | 252/529 |
| 4,046,717 | 9/1977 | Johnston | 252/546 |

FOREIGN PATENT DOCUMENTS 113887 11/1972 Japan .

Primary Examiner—Dennis L. Albrecht
Attorney, Agent, or Firm—Schmidt, Johnson, Hovey & Williams

[57] ABSTRACT

A toilet bar is provided containing either soap or a synthetic detergent as a cleansing agent and wherein an alkali metal salt of an acyl lactylate or glycolate is incorporated in the bar as a skin conditioning member which imparts a non-oily, talc-like, silky, very smooth, non-powdery feel to the user's skin. The preferred skin conditioning member is from about 1% to about 5% by weight of sodium isostearoyl lactylate incorporated in the bar.

6 Claims, No Drawings

SKIN CONDITIONING TOILET BAR

TECHNICAL FIELD

This invention relates to toilet bars having either soap or a synthetic detergent as the base material and which includes an additive that has the unique property of functioning as a skin conditioner which imparts to the user's skin a non-oily, talc-like, silky, very smooth, non-powdery feel following rinsing and drying.

BACKGROUND ART

The art of manufacturing toilet bars from soap and synthetic detergents is highly developed and for the most part involves extrusion of the material in plastic form as a ribbon which is cut into blanks that are in turn formed into tablets or bars using pressure molds of required configuration. Various additives are incorporated into the basic cleansing agent to increase the plasticity of the composition, provide a desirable fragrance, in many instances provide bacteriostatic action, and oftentimes to give skin conditioning effects which offset the harshness of the detergent or soap. Most skin conditioners, however, and especially those of the emollient oil type, leave a residue on the user's skin which tends to be oily in character and does not have a desirable after feel. These emollient oils also have the undesirable characteristic of suppressing foam during lathering. Even these additives though, often fail to alleviate skin conditions attributable to the harshness of the cleansing agent and therefore a need has long existed for a toilet bar additive which is non-irritating, has skin conditioning properties, is fully compatible with the base material of the bar as well as other materials normally incorporated therein, may be used at a reasonable cost, and has no undesirable odor or color problems associated therewith.

DISCLOSURE OF INVENTION

It is, therefore, the primary object of the present invention to provide a toilet bar having enhanced skin conditioning properties by incorporating an additive in the soap or synthetic detergent cleansing agent which comprises an acyl lactylate that is compatible with the user's skin and imparts a non-oily, talc-like, silky, very smooth, non-powdery feel after rinsing and drying.

Another important object of the invention is to provide a toilet bar wherein the skin conditioning additive added to the soap or synthetic detergent is preferably selected from the group of fatty acid lactylates and glycolates of the formula

wherein RCO is the acyl radical of a fatty acid of from 10 to 22 carbon atoms, A is $CH_3$ or H, x is a number from 1 to 4, and their alkali metal and physiologically acceptable amine salts. These additives have unexpectedly been found to give an improved after feel following use of the toilet bar without attendant dermatological reactions or interference with the cosmetic appearance of the product.

A further important object of the invention is to provide a toilet bar as described wherein the most beneficial results from the standpoint of skin conditioning are obtained by adding sodium isostearoyl lactylate or glycolate to the cleansing agent thereby providing enhanced conditioning of the skin under varying user demands.

Also an object of the invention is to provide a toilet bar where the non-irritating skin conditioning agent providing desirable after feel does not have a foam suppressing effect on the soap or synthetic detergent.

BRIEF DESCRIPTION OF INVENTION

It has now been discovered that by incorporating into either a soap or synthetic detergent toilet bar from about 1% to about 5% by weight of an acyl lactylate or glycolate produced by the reaction of a fatty acid having from 10 to 22 carbons atoms with lactic or glycolic acid, followed by formation of a salt of the ester, the after feel from use of the bar following rinsing and drying is unexpectedly better than when conditioning agents used in the past are incorporated in the product. Best results have been obtained using alkali metal acyl lactylates or glycolates which are produced from a branched chain fatty acids such as isostearic acid, or from blends or acyl lactylates made from fatty acids having 10 to 22 carbon atoms. The skin conditioning additive may be readily added to the soap or synthetic detergent at the time of preparation of the material for extrusion without modifying the normal production procedures or requiring expenditures for additional production equipment.

BEST MODE FOR CARRYING OUT THE INVENTION

The toilet bar of this invention normally contains on a percent by weight basis, from about 40% to about 90% of a cleansing agent which is physiologically acceptable to the skin and is selected from the group consisting of non-liquid anionic and aliphatic nonionic synthetic detergents which exhibit surface active characteristics and have required lathering properties, soaps selected from the group consisting of alkali metal, ammonium and alkanolamine salts of fatty acids containing from 8 to 24 carbon atoms, and combinations of the cleansing materials described. An exemplary soap has fatty components of 80% to 85% tallow and 20% to 15% coconut oil while numerous anionic and aliphatic nonionic synthetic detergents may be employed as the cleansing agent. For instance, the coconut oil acid ester of sodium isethionate gives particularly good results when used as the base of a synthetic detergent toilet bar.

The skin conditioning additives unexpectedly found to be useful in toilet bars may be added to various synthetic detergent products with exemplary synthetic detergents for example being disclosed in U.S. Pat. No. 3,523,089 comprising anionic surfactants of the so-called sulfated oil type. N-acyl sarcosinates are equally useful in the anionic category, as are the olefin sulfonates and sodium alkyl sulfates such as sodium lauryl sulfate. As previously indicated, ester and amide sulfonates may be used in synthetic detergent toilet bars. These compounds comprise sulfonates with an intermediate ester or amide group between the long hydrophobic chain and the sulfonate group and are usually produced by the reaction of the acid chloride of oleic acid with sodium isethionate or N-methyltaurine. Igepon A, $CH_3(CH_2)_7CH=CH(CH_2)_7CO_2C_2H_4SO_3Na$, or Igepon T, $CH_3(CH_2)_7CH=CH(CH_2)_7CON(CH_3)C_2H_4SO_3Na$ are exemplary. Other examples of useful anionic or aliphatic nonionic synthetic detergent products are found in Bailey's Industrial Oil and Fat Products, edited by Daniel Swern, 3rd Edition, 1964, distributed by the Interscience Publishers Division of John Wiley & Sons.

Most major soap plants of the world limit their soap production to essentially 80/20 tallow/coconut oil fatty components or within the 80 to 85 and 20 to 15 percent range of the specified constituents. All soaps of this character are useful in carrying out the novel concepts of this invention.

The skin conditioning acyl lactylate or glycolate comprises the esterification product of a fatty acid with a short chain hydroxy carboxylic acid and has the generic formula

$$RCO(OCHCO)_xOH$$
with A above the CH as substituent wherein RCO is the acyl radical of a fatty acid of from 10 to 22 carbon atoms, A is $CH_3$ or H, x is a number from 1 to 4, and their alkali metal and physiologically acceptable amine salts. Reference is made to U.S. Pat. Nos. 2,733,252; 2,789,992; 2,744,825; 2,744,826; and 3,728,447, which are expressly incorporated herein by reference thereto, for procedures for manufacturing acyl lactylates and glycolates within the definition and utility of this invention. Especially useful results have been obtained using sodium isostearoyl lactylate or glycolate. Very satisfactory results have been found using sodium stearoyl lactylate or glycolate, a 50—50 blend of sodium capryl lactylate or glycolate and sodium lauroyl lactylate or glycolate, a 50—50 as well as a 70-30 blend of sodium lauroyl lactylate or glycolate and sodium myristoyl lactylate or glycolate, a 50—50 blend of sodium stearoyl lactylate or glycolate and sodium oleoyl lactylate or glycolate. Among these products, the best results are obtained with sodium isostearoyl lactylate, better results are obtained employing sodium capryl lactylate or glycolate alone, or in combination with sodium lauroyl lactylate or glycolate, while good results are obtained with sodium stearoyl lactylate. A blend of triethanolamine lauroyl lactylate or glycolate with triethanolamine myristoyl lactylate and glycolate have also been demonstrated to be useful in providing skin conditioning effects in soap or synthetic detergent toilet bars. The skin conditioning agent is preferably added in an amount to provide 1% to 5% by weight thereof in the final product with the cleansing agent being from about 40% to about 90% of the composition while the remainder is primarily water, usually within the range of from about 4% to about 25%.

EXAMPLE 1

| SYNTHETIC DETERGENT TOILET BAR | | |
|---|---|---|
| | Range Per Cent by Weight | Preferred Per Cent by Weight |
| Coconut oil acid ester of sodium isethionate (Igepon AC-78) | 50–85 | 62 |
| Ethylene oxide polymer (polyox WSR-100 or 301) | 1–4 | 1 |
| Cellulose starch | 0–40 | 15 |
| Alkanolamide ($C_{10}$ or $C_{12}$ fatty acid amide) | 0–10 | optional |
| Titanium dioxide | 0–3 | 3 |
| Acyl lactylate (preferably | | |

| SYNTHETIC DETERGENT TOILET BAR -continued | | |
|---|---|---|
| | Range Per Cent by Weight | Preferred Per Cent by Weight |
| sodium isostearoyl lactylate) | 1–5 | 3 |
| Perfume | 0–4 | 2 |
| Methyl paraben | 0–1 | .2 |
| Propyl paraben | 0–2 | .2 |
| Water | 4–25 | 13.6 |

EXAMPLE 2

| SOAP TOILET BAR | | |
|---|---|---|
| | Range Per Cent by Weight | Preferred Per Cent by Weight |
| Sodium soap containing a ratio of 80/20 tallow to coconut oil fatty component | 50–85 | 77.8 |
| Titanium dioxide | 0–3 | 2 |
| Perfume | 0–4 | 2 |
| Water | 4–25 | 15 |
| Acyl lactylate (preferably sodium isostearoyl lactylate) | 1–5 | 3 |
| Preservative (methyl paraben, propyl paraben or combinations thereof) | 0–1 | 0.2 |

In these examples, additional pigments for aesthetics, stabilizers, slip agents, foam boosters, and conventional toilet bar additives may be incorporated in the formulation if desired.

Panel test studies have confirmed that the incorporation of an acyl lactylate such as sodium isostearoyl lactylate at a level of about 3 percent by weight in both soap and synthetic detergent toilet bars provides skin conditioning effects that are not obtainable with additives previously used. This expert panel of trained observers consisting of cosmetic chemists dealing daily with the formulation and evaluation of soap and synthetic detergent toilet bars (all of whom were associated with the major manufacturers and marketers of such toilet bars) reported positive effects with only one exception. The panel was comprised of 15 observers from 15 separate manufacturing and marketing organizations. In each instance, the observer washed one hand with a control bar that did not contain sodium isostearoyl lactylate, while the other hand was washed with a soap bar or synthetic detergent bar containing an additive of this invention (sodium isostearoyl lactylate present at a level of 3 percent by weight of the bar). No foam suppression was observed. Each hand was rinsed thoroughly with water and then dried. The feel of the skin was evaluated after 10 to 15 minutes by rubbing the fingers together of each hand. In the case of the bars which included sodium isostearoyl lactylate, all individuals of the test panel with the one exception noted found that the hand washed with the toilet bar containing the additive described herein gave very slight tack as noted during the drying period of the test which was deemed to be indicative of a residual layer of skin conditioning material on the user's skin. The same feel was not obtained with the control bar. Although all panelists concluded that the skin conditioning effect of a non-oily, talc-like, silky, very smooth, non-powdery feel was obtained with both types of bars containing sodium isostearoyl lactylate, the majority of the panel members felt that the effect was more pronounced in synthetic detergent bars than soap bars. Specifically, they concluded that there was a reduction of scroop in the case of synthetic detergent bars and this, of course, is an important feature of the skin conditioning effect of this invention, in that scroop is one of the major drawbacks associated with use of synthetic detergent toilet bars, especially under acid pH conditions. In this connection, it is to be recognized that synthetic detergents useful for toilet bars may be said to have the following necessary properties or characteristics. First, the detergent must be of the nonionic or anionic type, it must be available in non-liquid form, i.e. a powder flake or semi-solid, the material must act as a surfactant, it should exhibit adequate cleansing properties, be physiologically acceptable, i.e. non-irritating to the skin, a non-soap, and have satisfactory lathering and bubbling properties. In all instances, the sodium isostearoyl lactylate when added to synthetic detergent toilet bars of the properties described above, gave enhanced skin feel over control bars which did not include the lactylate additive.

Having thus described the invention, what is claimed as new and desired to be secured by Letters Patent is:

1. A toilet bar having enhanced skin conditioning properties by imparting to the user's skin a non-oily, talc-like, silky, very smooth, non-powdery feel and comprising a solid compressed form containing, on a percent by weight basis:
   (a) from about 40% to about 90% of a cleansing agent which is physiologically acceptable to the skin and selected from the group consisting of (1) solid anionic and aliphatic nonionic synthetic detergents which are moldable into a solid bar and exhibit surface active characteristics and have required lathering properties, (2) soaps selected from the group consisting of alkali metal, ammonium and alkanolamine salts of fatty acids containing from 8 to 24 carbon atoms, and (3) combinations thereof;
   (b) from about 1% to about 5% of at least one skin conditioning member compatible with said cleansing agent and selected from the group consisting of alkali metal isostearyl lactylate or glycolate and their physiologically acceptable amine salts; and
   (c) from about 4% to about 25% water.

2. A toilet bar as set forth in claim 1 wherein said synthetic detergent is a coconut oil acid ester of sodium isethionate.

3. A toilet bar as set forth in claim 1 wherein said soap is the salt of a fatty acid component of from about 80% to 85% tallow and about 20% to 15% coconut oil.

4. A toilet bar as set forth in claim 1 wherein said member is sodium isostearoyl lactylate or glycolate.

5. A toilet bar as set forth in claim 1 wherein said member is present in an amount of about 3%.

6. A method of imparting a non-oily, talc-like, silky, very smooth, non-powdery feel to a user's skin following cleansing with a toilet bar, said method comprising:
   (I) applying to the skin an effective amount of a cleansing composition from a solid compressed toilet bar, said bar containing on a percent by weight basis:
      (a) from about 40% to about 90% of a cleansing agent which is physiologically acceptable to the skin and selected from the group consisting of (1) solid anionic and aliphatic nonionic synthetic detergents which are moldable into a solid bar and exhibit surface active characteristics and have required lathering properties, (2) soaps selected from the group consisting of alkali metal, ammonium and alkanolamine salts of fatty acids containing from 8 to 24 carbon atoms, and (3) combinations thereof;
      (b) from about 1% to about 5% of at least one skin conditioning agent and selected from the group consisting of alkali metal isostearyl lactylate or glycolate and their physiologically acceptable amine salts; and
      (c) from about 4% to about 25% water; and
   (II) subsequently rinsing the skin with water.

* * * * *